US011266336B2

(12) United States Patent
Murphy et al.

(10) Patent No.: US 11,266,336 B2
(45) Date of Patent: Mar. 8, 2022

(54) ATTACHMENT MECHANISM TO ATTACH A COMPONENT TO A PARTICULAR LOCATION ON A TUBE IN A BLOOD SAMPLING-BLOOD PRESSURE MONITORING SYSTEM

(71) Applicant: Edwards Lifesciences Corporation, Irvine, CA (US)

(72) Inventors: Brian Patrick Murphy, Costa Mesa, CA (US); Tomy Tran, Roseville, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 277 days.

(21) Appl. No.: 16/418,419

(22) Filed: May 21, 2019

(65) Prior Publication Data

US 2019/0374142 A1     Dec. 12, 2019

Related U.S. Application Data

(60) Provisional application No. 62/683,115, filed on Jun. 11, 2018.

(51) Int. Cl.
*A61B 5/15* (2006.01)
*A61B 5/153* (2006.01)

(52) U.S. Cl.
CPC .... *A61B 5/15003* (2013.01); *A61B 5/150221* (2013.01); *A61B 5/150992* (2013.01); *A61B 5/153* (2013.01); *A61B 5/150351* (2013.01); *A61B 5/150389* (2013.01); *A61B 5/150572* (2013.01)

(58) Field of Classification Search
CPC ........ A61B 5/150221; A61B 5/150351; A61B 5/150389; A61B 5/150572; A61B 5/15992; A61B 5/153; A61B 5/15003; A61B 5/150267
See application file for complete search history.

(56) References Cited

U.S. PATENT DOCUMENTS

| | | | |
|---|---|---|---|
| 4,043,333 A | 8/1977 | Munsch | |
| 4,112,944 A | 9/1978 | Williams | |
| 5,002,066 A | 3/1991 | Simpson et al. | |
| 5,135,489 A | 8/1992 | Jepson et al. | |
| 5,197,708 A | 3/1993 | Campau | |
| 6,193,675 B1 * | 2/2001 | Kraus | A61B 5/155 600/576 |
| 6,216,723 B1 | 4/2001 | King | |
| 6,692,479 B2 | 2/2004 | Kraus et al. | |
| 6,773,036 B1 | 8/2004 | King | |

(Continued)

FOREIGN PATENT DOCUMENTS

WO     2014092910 A1     6/2014

*Primary Examiner* — Sean P Dougherty
*Assistant Examiner* — Kyle W. Kretzer
(74) *Attorney, Agent, or Firm* — Eric T King; Womble Bond Dickinson (57) ABSTRACT

An attachment mechanism is used to attach a component to a particular location on a tube in a blood sampling-blood pressure monitoring system by a user. The attachment mechanism may include a piercing feature. The piercing feature may be used to pierce the tube to attach the component to the particular location on the tube of the blood sampling-blood pressure monitoring system selected by the user.

12 Claims, 4 Drawing Sheets

(56) References Cited

U.S. PATENT DOCUMENTS

| | | | |
|---|---|---|---|
| 7,182,753 B2 | 2/2007 | Matsumoto | |
| 7,195,624 B2 | 3/2007 | Lockwood et al. | |
| 7,232,428 B1 | 6/2007 | Inukai et al. | |
| 7,435,231 B2 | 10/2008 | Mathias et al. | |
| 8,092,385 B2 | 1/2012 | Goldberger et al. | |
| 9,061,129 B2 | 6/2015 | Lauer | |
| 9,357,950 B2 | 6/2016 | Mendels et al. | |
| 9,775,981 B2 | 10/2017 | Nelson et al. | |
| 11,058,815 B2* | 7/2021 | Tallarida | A61M 1/3653 |
| 2007/0179407 A1* | 8/2007 | Gordon | A61B 5/15003 |
| | | | 600/584 |
| 2007/0179435 A1 | 8/2007 | Braig et al. | |
| 2008/0200837 A1 | 8/2008 | Frazier et al. | |
| 2009/0221933 A1* | 9/2009 | Nishtala | A61B 5/205 |
| | | | 600/561 |

\* cited by examiner

A TTACHMENT MECHANISM TO ATTACH A
COMPONENT TO A PARTICULAR
LOCATION ON A TUBE IN A BLOOD
SAMPLING-BLOOD PRESSURE
MONITORING SYSTEM

CROSS-REFERENCE TO RELATED
APPLICATIONS

This application claims the benefit of U.S. Provisional Patent Application No. 62/683,115 filed Jun. 11, 2018, which is incorporated by reference herein in its entirety.

BACKGROUND

Field

The present invention relates to an attachment mechanism, and, in particular, to an attachment mechanism to attach a component to a location on a tube in a blood sampling-blood pressure measurement system.

Relevant Background

In a hospital setting there is always the need to monitor patient health through the evaluation of a blood chemistry profile. The simplest method employed in the hospital is to use a syringe carrying a sharpened cannula at one end and insert that cannula into a vein or artery to extract a blood sample from the patient. Patients that are in critical care units or the operating room sometimes require as many as twelve samples a day. Such frequent sampling injections potentially expose the patient to airborne bacteria and viruses which can enter the bloodstream through the opening made by the sharpened cannula.

One way to obtain a blood sample is to draw the blood from a catheter that is already inserted in the patient, either in a central venous line, such as one placed in the right atrium, or in an arterial line. Typically, existing access sites for arterial or venous or pressure monitoring lines are used to take periodic blood samples from the patient. Conventional mechanisms for drawing blood from the lines used for infusion or pressure monitoring utilize a plurality of stopcock mechanisms that preclude flow from the infusion fluid supply or from the pressure column drip supply, while allowing blood to flow from the patient into a collecting syringe connected to a proximal port formed in one of the stopcocks.

Earlier systems required a two-step operation where a first sample of fluid, generally about 5 ml in volume for intensive care environments was withdrawn into the sampling syringe and discarded. This first sample potentially included some of the infusion fluid and thus would be an unreliable blood chemistry measurement sample. After the initial sample had been discharged, the second sample was pure blood from the artery or vein.

In response to the drawbacks associated with earlier two-step sampling systems, closed systems were developed. Commercial closed systems such as the Venous Arterial blood Management Protection (VAMP) system feature a reservoir in the tubing line from the patient that can draw fluid past a sampling port. The clearing volume is held in the in-line reservoir, and set-aside in a syringe for re-infusion later. The sampling systems are often used in conjunction with a pressure monitor having a transducer continuously or periodically sensing pressure within the sampling line except during the draw of a blood sample.

The VAMP system conveniently utilizes a reservoir with one-handed operability, and includes a line from the patient into and out of the reservoir and to a proximal source of flushing fluid and a pressure transducer. (The standard directional nomenclature is that proximal is toward the clinician, or away from the patient, and distal is toward the patient). A pressure transducer in the line proximal to the reservoir senses fluid pressure within the line and conveys the signal to a monitor. One exemplary pressure transducer is a Disposable Pressure Transducer (DPT).

When a blood sample is to be taken, the nurse or clinician withdraws an amount of fluid into the reservoir chamber and distal line sufficient to pull pure blood past one or more fluid sampling sites. After full retraction of the plunger, the stopcock valve closes off the reservoir from the patient and a sample of blood is taken at one or more of the sampling sites. Subsequently, the clinician manipulates the stopcock valve so that the volume within the reservoir can be re-infused back into the patient by depressing the plunger, and the flushing drip and pressure monitoring resumes.

In blood sampling and blood pressure monitoring systems, there is a clinical need for kits which contain varying tubing lengths and varying number of components. Many blood sampling and pressure monitoring systems have been developed and are on the market. Unfortunately, these blood sampling and blood pressure monitoring systems are pre-assembled at a manufacturing site and are not able to be customized by the user.

DETAILED DESCRIPTION

Figure 1:
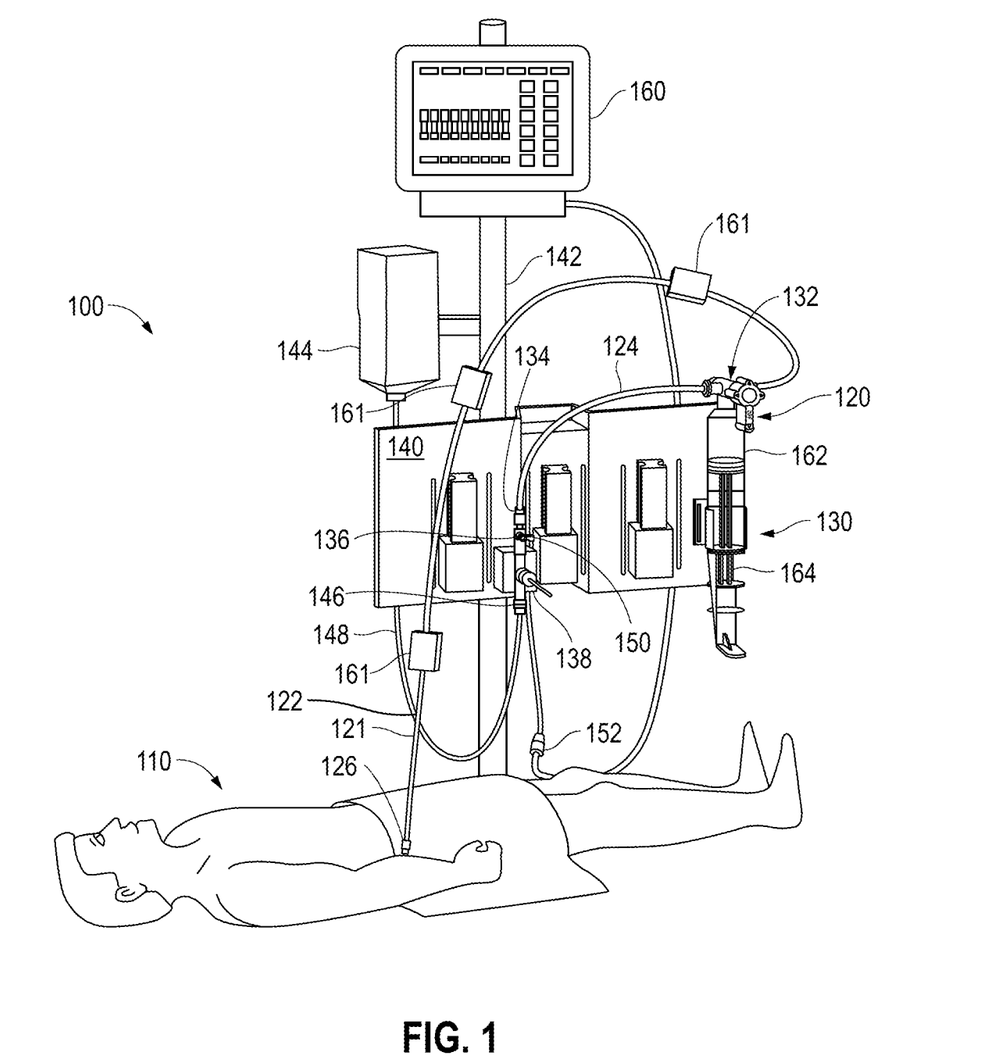
FIG. 1 is a diagram illustrating an example blood sampling-blood pressure monitoring system as may be set up in a hospital room that utilizes an attachment mechanism to attach a component at a particular desired location selected by a user, according to embodiments of the invention.

FIG. 1 illustrates an example blood sampling system 120 in an example blood sampling-blood pressure monitoring system 100 as may be set up in a hospital room and connected to a patient 110. The blood sampling system 120 comprises a conduit line or tube 122 having a distal segment 121 toward the patient 110 and a proximal segment 124. The distal segment 121 may terminate in a male luer connector 126 for attaching to a female luer connector (not shown) of an injection site, or other conduit leading to the patient 110. A reservoir 130 connects to the conduit line via a multi-port control valve 132 interposed between the distal segment 121 and the proximal segment 124. The multi-port control valve 132 externally resembles a stopcock and controls fluid flow between the conduit line and the reservoir 130.

The proximal segment 124 extends from the multi-port control valve 132 and terminates in a female luer connector 134 attached to a stopcock 136 of a pressure transducer 138 (e.g., a disposable pressure transducer (DPT)). The reservoir 130 and pressure transducer 138 removably mount to a bracket 140 which, in turn, may be secured to a conventional pole support 142 with the reservoir 130 in a vertical orientation.

As mentioned above, the blood sampling system 120 forms a portion of the blood sampling-blood pressure monitoring system 100, and the pressure transducer 138 may be a DPT. However, it should be appreciated that any type of pressure monitoring device may be utilized.

A supply of flush solution 144 connects to a flush port 146 of the transducer 138 via tubing 148. Typically, the flush solution 144 comprises a bag of physiological fluid such as saline surrounded by a pressurized sleeve that squeezes the fluid and forces it through the tubing 148. In addition, an infusion fluid supply (not shown) may be provided in communication with an infusion port 150 of the stopcock 136. The pressure transducer 138 is thus placed in fluid communication with the arterial or venous system of the patient 110 through the conduit line, and includes a cable and plug 152 to connect to a suitable display monitor (e.g., patient monitor 160). The pressure transducer 138 is shown positioned within the proximal segment 124.

As will be described, by using an attachment mechanism, various components 161 may be attached at particular locations on the tube or tubing 122 in the blood sampling-blood pressure monitoring system 100 as selected by the user.

As one example, the component 161 may be a fluid sampling site that includes a Z-shaped flow passage (or any creating a laminar or turbulent flow) adjacent a pre-slit septum that may be utilized to sample blood. The septum preferably comprises an elastomeric disc which accepts a blunt cannula and reseals after each sample is drawn, reducing the potential for contamination and eliminating the danger of needle sticks. However, any type of fluid sampling site may be utilized. Further, as will be described, any type of component 161 may be attached at a particular location on the tube 122 in the blood sampling-blood pressure monitoring system 100 as selected by the user utilizing the attachment mechanism. These types of adjustable position components that may be placed at desired particular locations by the user utilizing the attachment mechanism, include, but are not limited to: blood sample sites; blood pressure sensors; flow sensors; signal sensors; reservoirs; stopcocks; etc.

Continuing with the example of the blood sampling-blood pressure monitoring system 100, the blood sampling reservoir 130 may include a syringe-type variable volume chamber 162, though other reservoirs that have constant volume chambers or other receptacles for receiving fluid may be used. The reservoir 130 is of a type that includes a channel through the variable volume chamber 162 for passage of flushing fluid therethrough.

As an example, a clinician may rotate a valve handle of the multi-port control valve 132 to select a mode of operation (e.g., a monitoring mode, a drawing/re-infusing mode, a sampling mode, or a flushing/priming mode). In the monitoring mode, the pressure transducer 138 may continuously or periodically sense pressure within the sampling line to measure the patient's blood pressure and forwards the signal to the display monitor 160. In the drawing mode, the plunger 164 of the reservoir 130 may draw a fluid sample into the chamber 162 of the reservoir 130 to draw blood from the patient 110 past the sampling site 161. In the sampling mode, the clinician may take a sample of undiluted blood from the sampling site 161. In the re-infusing mode, the clinician may depress the plunger 164 to re-infuse blood and fluid from the reservoir 130 and tubes back to the patient 110. In the flushing/priming mode, the reservoir 130, sample sites 161, and tubes can be flushed, cleared, and de-bubbled such that portions of the blood sampling-blood pressure monitoring system 100 may be cleared for operation. In particular, in this mode, a supply of flush solution 144 connects to a flush port 146 of the transducer 138 via tubing 148 and can be flushed through the reservoir 130, sample sites 161, and tubes for flushing and clearing.

As an example, in the drawing mode a reduced pressure is created within the variable volume chamber 162 by withdrawing the plunger 164 such that a fluid sample from the distal segment 122 is drawn into the chamber 162. The chamber 162 may have a sufficient volume, e.g., 12 ml, to draw blood from the patient 110 past the sampling site 161. The clinician can then take a sample of undiluted blood from the sampling site 161. Subsequently, the blood and other fluids drawn into the reservoir 130 during the sampling operation may be re-infused by depressing the plunger 164. It should be noted that the pressure transducer 138 may include a flow restrictor or flow control means to prevent flushed solution from going proximally through the sensor rather than back to the patient 110. For example, the stopcock 136 may be used to close off the fluid path through the pressure transducer 138 prior to re-infusing the reservoir clearance volume. The entire sampling system 120 is thus closed as the "priming" volume that ensures a pure sample of blood reaches the sampling site 161 remains within the sampling system 120 and is re-infused into the patient. Further, in the flushing/priming mode, the reservoir 130, sample sites 161, and tubes can be flushed, cleared, and de-bubbled such that portions of the blood sampling-blood pressure monitoring system 100 may be cleared for operation, as previously described.

As has been described above, with respect to FIG. 1, an example of a blood sampling-blood pressure monitoring system 100 has been illustrated. In particular, as has been described, the blood sampling-blood pressure monitoring system 100 may include: a control valve 132, a blood pressure transducer 138, a reservoir 130 with a plunger 164, a sampling site 161, and a blood pressure transducer 138 for measuring the blood pressure of the patient 110, which may be displayed on the display monitor 160. Further, as has been described, a tube may be connected from the patient 110 to the sampling site 161, from the sampling site 161 to the control valve 132, and from the control valve 132 to the pressure transducer 138, etc. In one embodiment, the control valve 132 may be a multi-port control valve that is described in detail in pending U.S. patent application Ser. No. 15/801,009, entitled "Multi-Port Control Valve for use in a Blood Sampling, Blood Pressure Measurement Systems", hereby incorporated by reference, or may be any suitable control valve presently utilized in blood sampling-blood pressure monitoring systems.

Also, it should be appreciated that blood sampling site 161 has been referred to as an example of one of the components 161. However, a wide variety of different components 161 (including blood sampling site components) may be placed at desired particular locations selected by the user utilizing the attachment mechanism, as will be described, including, but not limited to: blood sample sites; blood pressure sensors; flow sensors; signal sensors; reservoirs; stopcocks; etc.

Aspects of the invention may be considered to relate to new systems for minimally invasive blood sampling and blood pressure monitoring systems that include adjustable position components that may be attached at particular desired locations on a tube by a user utilizing attachment mechanisms. These types of adjustable position components may include, but are not limited to: blood sample sites; blood pressure sensors; flow sensors; signal sensors; reservoirs; stopcocks; etc.

As an example, a user may be able to assemble a kit for components of blood sampling-blood pressure monitoring system 100, when they receive the kit, to their own exact particular specifications. For example, a component 161, such as, a sample site, pressure sensor, or other stand-alone component, may be attached to the tubing 122 by piercing the tubing 122 in order to redirect the flow of blood and saline to the component, at a particular location, selected by the user, utilizing an attachment mechanism to be hereafter described. This allows for great flexibility in the positioning of components as desired by user—as compared to existing pre-assembled products. In particular, traditional blood pressure sampling and monitoring products are assembled at a manufacturing site and are not able to be customized by a user.

In one embodiment, an attachment mechanism to attach a component 161 to a particular location on the tube 122 in the blood sampling-blood pressure monitoring system 100 by a user, will be described. The attachment mechanism may comprise a piercing feature. The piercing feature may be used to pierce the tube 122 to attach the component 161 to the particular location selected by the user on the tube 122 of the blood sampling-blood pressure monitoring system 100. It should be appreciated that the component 161 may include: a blood sampling site; a blood pressure sensor; a flow sensor; a signal sensor; a reservoir; a stopcock; etc. It should be appreciated that any type of component 161 utilized in a medical environment may be utilized.

Figure 2:
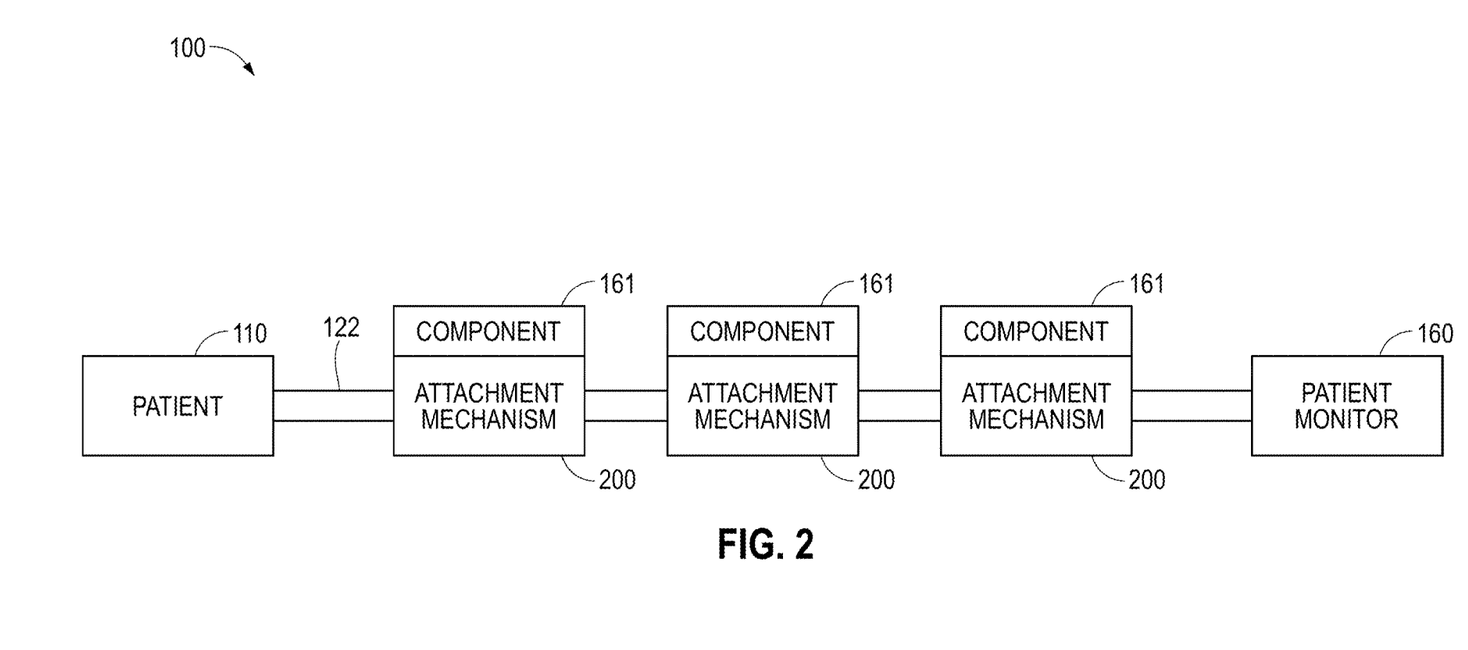
FIG. 2 is a diagram particularly illustrating an attachment mechanism to attach a component to tubing, according to embodiments of the invention.

With additional reference to FIG. 2, an example of a blood sampling-blood pressure monitoring system 100, utilizing embodiments of the invention, will be described. As can be seen in FIG. 2, which, is a simplification of previously described FIG. 1, a patient 110 may be connected to various components 161 of the blood sampling-blood pressure monitoring system 100 through tubing 122 and the physiological aspects of the patient 110 may be monitored by the patient monitor 160. In particular, as shown in FIG. 2, an attachment mechanism 200 may be utilized to attach each of the components 161 to a particular desired location selected by a user on the tube 122 of the blood sampling-blood pressure monitoring system 100.

As can be seen in FIG. 2, a plurality of components 161 may be attached at various locations on tubing 122 of the blood sampling-blood pressure monitoring system 100 via an attachment mechanism 200. As has been described, the components 161 may include such items as: a blood sampling site; a blood pressure sensor; a flow sensor; a signal sensor; a reservoir; a stopcock; etc. In this way, as has been described, a user may be able to assemble a kit when they receive it to their own exact particular specification for their blood sampling-blood pressure monitoring system. For example, a blood sample site component 161, a pressure sensor component 161, or other stand-alone component 161, may be attached by the attachment mechanism 200 at a user desired location on the tubing.

As an example, the attachment mechanism 200 may include a piercing feature that pierces the tube 122 to attach the component 161 to the particular location selected by the user on the tube 122 of the blood sampling-blood pressure monitoring system 100. This allows for greater flexibility in positioning the location of components 161—as compared to existing pre-assembled products. Further, as an example, the piercing feature may include a pair of needles that each fully block opposite orifices of the tubing 122 and redirect the flow of fluid from the tube 122 to the component 161.

Therefore, as shown in FIG. 2, a user may be able to attach various components 161 via attachment mechanisms 200 to particular locations on tubing 122 to assemble their own desired blood sampling-blood pressure monitoring system 100 to their own exact particular specification. As will be described, in one embodiment, the attachment mechanism 200 may include a piercing feature that may include a pair of needles that each fully block orifices of the tubing 122 and redirect the flow of fluid from the tube 122 to the component 161. For example, the component 161 may be blood sampling site and the attachment mechanism may pierce the tubing 122 in order to redirect the flow of blood and saline under the septum of the sample site 161 to obtain blood samples.

Various examples of attachment mechanisms 200 will be hereafter described.

Figure 3A:
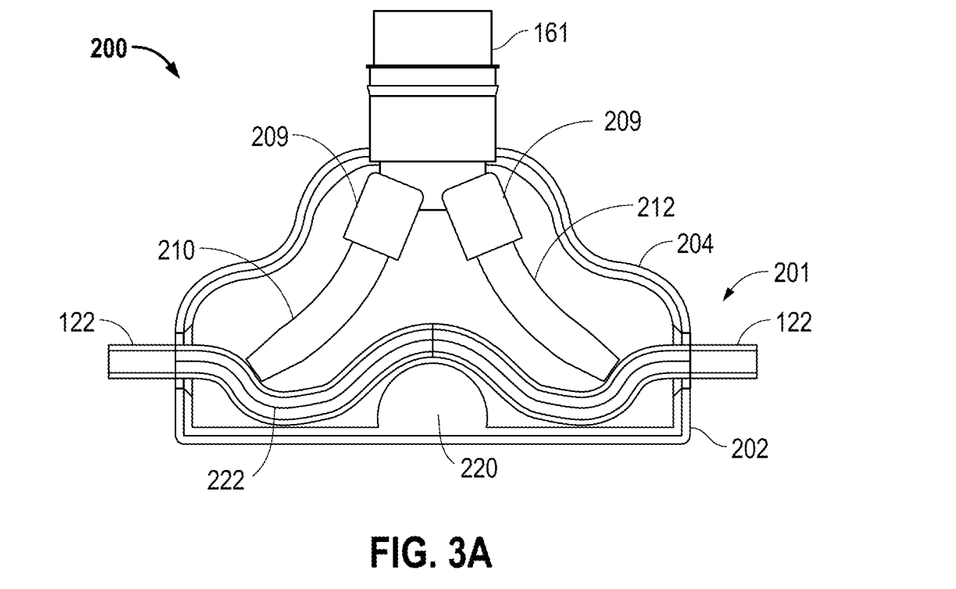
FIGS. 3A-3B are diagrams illustrating an attachment mechanism that comprises a piercing feature that includes a pair of needles, according to embodiments of the invention.
Figure 3B:
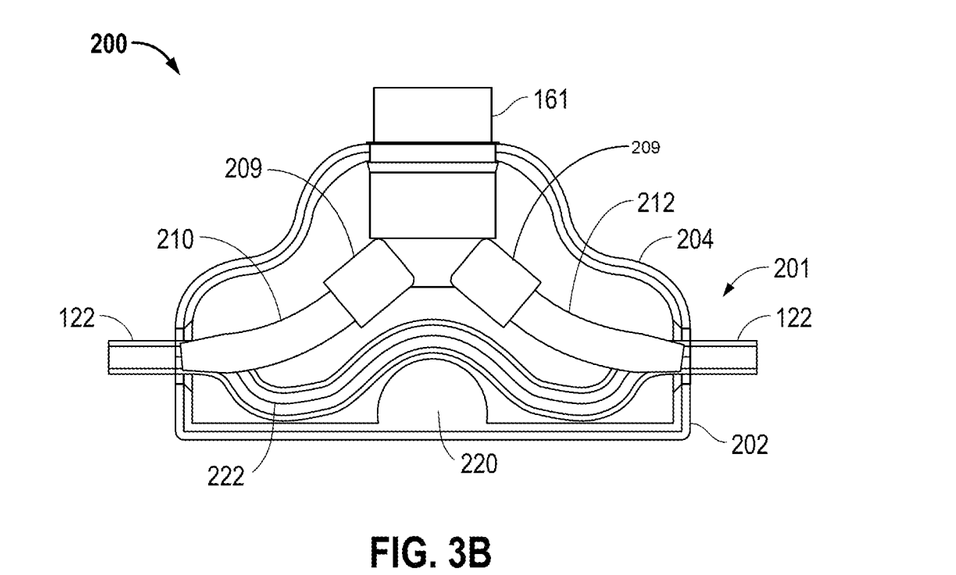

With reference to FIGS. 3A-3B, one type of attachment mechanism 200 may include a piercing feature that comprises a pair of needles 210 and 212. The pair of needles 210 and 212 may each be connected to the component 161 by suitable rotatable connectors 209 and further the pair of needles 210 and 212 may be flexible and rotatable, as shown in FIGS. 3A-3B. As will be described, when connected, the pair of needles 210 and 212 each fully block opposite orifices of the tubing 122 and redirect the flow of fluid from the tubing 122 to the component 161 (see FIG. 3B).

As an example, component 161 may be a blood sampling site. The piercing feature pierces the tubing 122 and redirects the flow of fluid (e.g., blood) to the component 161. As an example, in the blood sampling site component 161 implementation, blood may be redirected to the septum of the blood sampling site. As can be seen in FIG. 3B, the pair of needles 210 and 212 each fully block the orifice of the tubing 122 and redirect the flow of blood to the blood sampling site 161 above.

In one type of implementation, the piercing feature of the attachment mechanism 200 may comprise a housing 201 having a top block 204 and a bottom block 202. The top block 204 mounts component 161 and the pair of needles 210 and 212 connected to the component 161. The top block 204 of the housing 201 may be placed over and surround the top part of the tube 122 and the bottom block 204 of the housing 201 may be placed under and surround the bottom part of the tube 122. The top and bottom blocks 204, 202 may be pushed together such that the housing 201 surrounds the tube 122 and the pair of needles 210 and 212 are inserted into the orifices of the tubing 122 and block orifices of the tubing 122 on each side and redirect the flow of fluid into and out the component 161.

In particular, as shown in FIGS. 3A-3B, when the top and bottom blocks 204, 202 of the housing 201 are compressed together, a circular bottom portion 220 of the bottom block 202 of the housing 201 pushes the internal part 222 of tubing 122 upward such that the tubing forms a wave shape and the pair of needles 210 and 212 are pushed against the tubing 122 and are rotated to pierce the tubing 122 and extend through sides of the housing 201 such that they are each fully inserted into the opposite orifices of the tubing 122 on opposite sides so that they block the orifices of the tubing 122 on each side and redirect the flow of fluid into and out of the component 161.

Therefore, in this implementation, fluid in tubing 122 is completely redirected through needles 210 and 212 into and out of the component 161. In this way, component 161 can be attached to the tubing 122 at a particular desired location by a user of the blood sampling-blood pressure monitoring system. As previously described, such components 161 may be blood sampling sites, blood pressure sensors, flow sensors, signal sensors, reservoirs, stopcocks, etc.

Figure 4A:
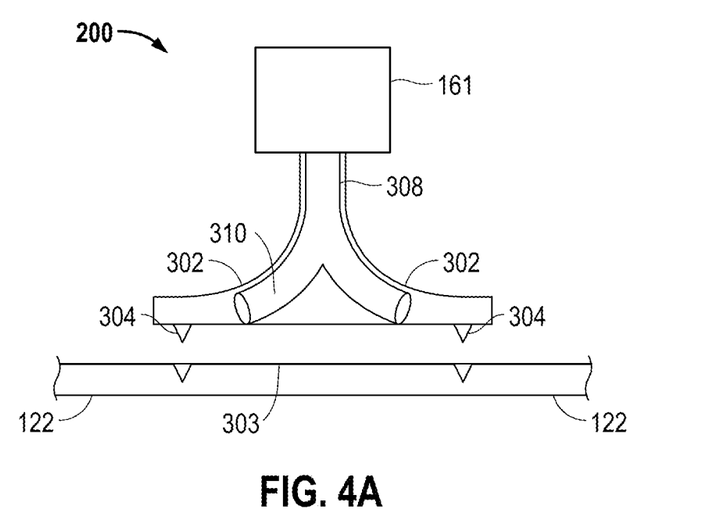
FIGS. 4A-4B are diagrams illustrating an attachment mechanism that includes a guillotine mechanism, according to embodiments of the invention.
Figure 4B:
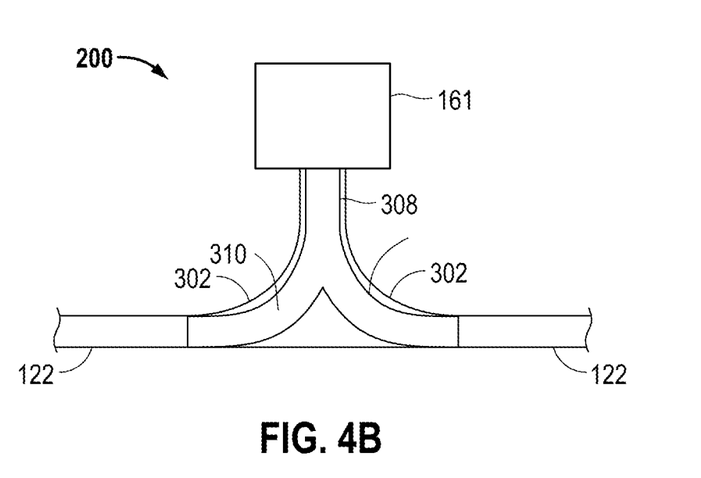

With additional reference to FIGS. 4A-4B, in another embodiment, a component 161 may be attached with an attachment mechanism 200 that likewise includes a piercing feature. In this embodiment, the piercing feature utilizes a guillotine mechanism.

In this embodiment, a piece of tubing 122 may be cut out entirely and the fluid path of the tubing 122 may be resealed through friction. As one example, a piece of tubing 122 may be cut out entirely by razors and the guillotine mechanism is compressed down with a replacement tube section with internal tubes connected to the component such that the fluid path of the tubing 122 is resealed through friction and the tubing 122 is connected to the component 161.

As a particular example, as can be seen in FIGS. 4A-4B, the piercing feature may include a guillotine mechanism including razors 304, a replacement tube section 302, and an internal tubing section 308 having a pair of internal needles 310. The internal tubing section 308 being connected to the component 161. In this implementation, a tubing section 303 of tubing 122 is cut out entirely by razors 304 and replaced by the replacement tube section 302. As an example, after inserting the replacement tube section 302, the internal tubing section 308 and pair of internal needles 302 are compressed downward such that the pair of internal needles 310 extend into the openings of the existing tubing 122. In particular, the replacement tubing section 302 is connected to the tubing 122 via friction by the pair of needles 310 of the internal tubing 308 being fully inserted into the orifices of the tubing 122 on opposite sides such that they block and are fully inserted into the orifices of the tubing 122 on each side and redirect the flow of fluid from the tubing 122 via the needles 310 and the internal tubing section 308 to the component 161.

Therefore, in this implementation, fluid in tubing 122 is completely redirected through needles 310 into and out of the component 161. In this way, component 161 can be attached to the tubing 122 at a particular desired location by a user of the blood sampling-blood pressure monitoring system. As previously described, such components 161 may be blood sampling sites, blood pressure sensors, flow sensors, signal sensors, reservoirs, stopcocks, etc.

Figure 5:
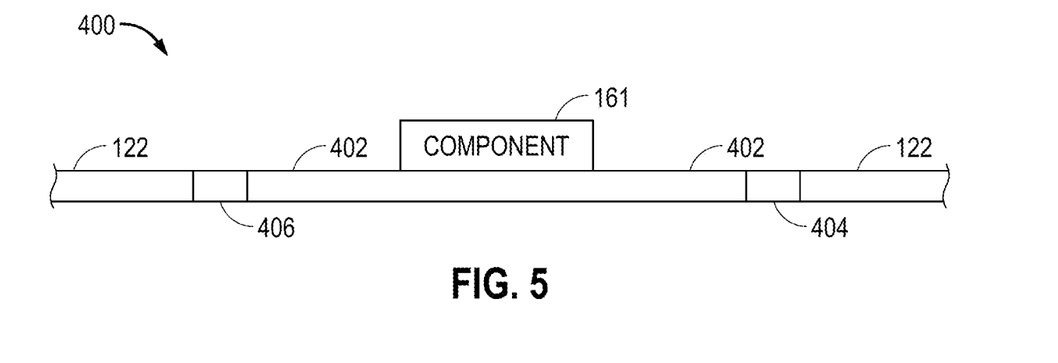
FIG. 5 is a diagram illustrating an attachment mechanism to attach a component to tubing, according to embodiments of the invention.

With additional reference to FIG. 5, another type of attachment mechanism that utilizes a piercing feature to pierce the tubing may be an automated machine method 400. In this embodiment, a user may utilize a standard cutting machine to cut out an existing small tubing section of the tubing 122. After, cutting out the existing small tubing section, a new tubing section 402 may be inserted between the existing tubing sections of tubing 122. The new tubing section 402 includes an attached component 161. In this way, the attached component 161 with the new tubing section 402 may be inserted at a particular desired location selected by the user. As an example, at points 404 and 406, the new tubing section 402 with the component 161 may be bonded to the existing tubing 122. In this way, as previously described, by bonding the new tubing section 402 to the existing tubing section 122, fluid flow may be redirected to the component 161. Therefore, in this implementation, fluid in tubing 122 is now directed to component 161 with the inserted tubing section 402. In this way, component 161 can be attached to the tubing 122 at a particular desired location by a user of the blood sampling-blood pressure monitoring system. As previously described, such components 161 may be blood sampling sites, blood pressure sensors, flow sensors, signal sensors, reservoirs, stopcocks, etc.

Similarly, as another example, a movable piece including a component and a new tubing section may be used, in which the new tubing section includes a pair of male and female connectors at each end. In this implementation, the existing tubing 122 is simply cut at a particular desired location by the user and the new tubing section with the component 161 attached thereto is placed therein with the pair of male and female connectors at each end being inserted into the existing tubing 121. In this way, as previously described, fluid in tubing 122 is now directed to component 161 with the inserted new tubing section. As previously described, such components 161 may be blood sampling sites, blood pressure sensors, flow sensors, signal sensors, reservoirs, stopcocks, etc.

It should be appreciated that according to the previously described attachment mechanisms and methods that any type of component 161 may be attached to a particular location selected by the user to the tube 122 in the blood sampling-blood pressure monitoring system 100 via the previously described techniques. These components 161 may include such items as: a blood sampling site; a blood pressure sensor; a flow sensor; a signal sensor; a reservoir; a stopcock; or any suitable device associated with a medical environment.

It should be appreciated that by utilizing the above assembly features, a user may be able to assemble their kit for blood pressure monitoring and sampling, when they receive it—to their own exact particular specification. In this type of example, the blood sample site, blood pressure sensor, or other stand-alone component, may be attached to the tubing 122 by piercing the tubing in order to redirect the flow of blood and saline to the component 161. This allows for greater flexibility in selecting the position of components on the tubing 122—as compared to existing pre-assembled products. In this way, these adjustable systems may utilize different configurations of blood sampling sites, reservoirs, blood pressure transducers, stopcocks, or other types of components, all of which may be adjustable as to positioning/location on the tubing 122. In this way, the user may be able to assemble their kit when they receive it to their own desired specifications.

Further, it should be appreciated that although these types of techniques have been illustrated with respect to a blood sampling-blood pressure monitoring system, it should be appreciated that these techniques may be implemented with any type of medical system or any type of system (medical or non-medical) that utilizes tubing, fluid flow, and components associated with fluid.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. An attachment mechanism to attach a component to a particular location on a tube in a blood sampling-blood pressure monitoring system by a user, the attachment mechanism comprising:

a piercing feature, wherein, the piercing feature pierces the tube to attach the component to the particular location on the tube of the blood sampling-blood pressure monitoring system selected by the user, the piercing feature including a housing that surrounds the tube and a pair of needles that each fully inserts into opposite orifices of the tube on opposite sides and fully block the tube on each side and redirects a flow of fluid from the tube to the component.

2. The attachment mechanism of claim 1, wherein the component includes a blood sampling site.

3. The attachment mechanism of claim 1, wherein the component includes at least one of a blood sampling site, a blood pressure sensor, a flow sensor, a signal sensor, a reservoir, or a stopcock.

4. The attachment mechanism of claim 1, wherein the housing surrounds the tube with a bottom block that pushes the tube upwards making the tube form a wave shape such that the pair of needles each fully insert into the orifices of the tube on the opposite sides and block the tube on each side and redirect the flow of fluid to the component.

5. A blood sampling-blood pressure monitoring system comprising:
   a tube connected to a patient;
   a blood pressure sensor coupled to the tube to sense the patient's blood pressure;
   a monitor to display the patient's blood pressure based upon an input from the blood pressure sensor; and
   an attachment mechanism to attach a component to a particular location on the tube, the attachment mechanism including a piercing feature, wherein, the piercing feature pierces the tube to attach the component to the particular location on the tube selected by a user, the piercing feature including a housing that surrounds the tube and a pair of needles that each fully inserts into opposite orifices of the tube on opposite sides and fully blocks the tube on each side and redirects a flow of fluid from the tube to the component.

6. The blood sampling-blood pressure monitoring system of claim 5, wherein the component includes a blood sampling site.

7. The blood sampling-blood pressure monitoring system of claim 5, wherein the component includes at least one of a blood sampling site, a blood pressure sensor, a flow sensor, a signal sensor, a reservoir, or a stopcock.

8. The blood sampling-blood pressure monitoring system of claim 5, wherein the housing surrounds the tube with a bottom block that pushes the tube upwards making the tube form a wave shape such that the pair of needles each fully insert into the orifices of the tube on the opposite sides and block the tube on each side and redirect the flow of fluid to the component.

9. A method to attach a component to a particular location on a tube in a blood sampling-blood pressure monitoring system by a user, the method comprising:
   selecting the particular location on the tube by the user;
   attaching the component at the particular location with an attachment mechanism, the attachment mechanism including a piercing feature, wherein, the piercing feature pierces the tube to attach the component to the particular location on the tube of the blood sampling-blood pressure monitoring system, the piercing feature including a housing that surrounds the tube and a pair of needles that each fully inserts into opposite orifices of the tube on opposite sides and fully blocks the tube on each side and redirects a flow of fluid from the tube to the component.

10. The method of claim 9, wherein the component includes a blood sampling site.

11. The method of claim 9, wherein the component includes at least one of a blood sampling site, a blood pressure sensor, a flow sensor, a signal sensor, a reservoir, or a stopcock.

12. The method of claim 9, wherein the housing surrounds the tube with a bottom block that pushes the tube upwards making the tube form a wave shape such that the pair of needles each fully insert into the orifices of the tube on the opposite sides and block the tube on each side and redirect the flow of fluid to the component.

* * * * *